(12) United States Patent
Shigemitsu et al.

(10) Patent No.: US 7,671,219 B2
(45) Date of Patent: Mar. 2, 2010

(54) METHOD FOR MANUFACTURING FULLERENE DERIVATIVES

(75) Inventors: Yasuo Shigemitsu, Saitama (JP); Yusuke Tajima, Saitama (JP)

(73) Assignee: Institute of Medicinal Molecular Design, Inc., Tokyo (JP)

( * ) Notice: Subject to any disclaimer, the term of this patent is extended or adjusted under 35 U.S.C. 154(b) by 266 days.

(21) Appl. No.: 11/569,571

(22) PCT Filed: May 26, 2005

(86) PCT No.: PCT/JP2005/009653

§ 371 (c)(1),
(2), (4) Date: Aug. 14, 2007

(87) PCT Pub. No.: WO2005/116006

PCT Pub. Date: Dec. 8, 2005

(65) Prior Publication Data

US 2008/0139826 A1 Jun. 12, 2008

(30) Foreign Application Priority Data

May 28, 2004 (JP) .............................. 2004-159095

(51) Int. Cl.
*C07D 307/94* (2006.01)
*C07D 317/72* (2006.01)
*C07D 317/70* (2006.01)
*C07D 317/44* (2006.01)

(52) U.S. Cl. ...................... 549/334; 549/341; 549/432

(58) Field of Classification Search ................. 549/430, 549/448
See application file for complete search history.

(56) References Cited

FOREIGN PATENT DOCUMENTS

JP 2003-277373 10/2003

OTHER PUBLICATIONS

Y. Tajima et al.: Highly Efficient Acetalization of Epoxide Groups on Fullerene. XP00300707, Jul. 28, 2004, vol. 27, p. 161.
C.S. Foote, NATO ASI Series C: Mathematical and Physical Sciences, 1994, vol. 443, pp. 79-96.
Y. Elemes et al., Angewandte Chemie, 1992, vol. 104, No. 3, pp. 364-366.
G.-W. Wang et al., Journal of the Chemical Society, Chemical Communications, 1995, vol. 10, pp. 1071-1072.
M. Yoshida et al., Tetrahedron Letters, 1993, vol. 34, No. 47, pp. 7629-7632.
S.-B. Lee et al., Chemistry Letters, 1990, vol. 11, pp. 2019-2022.
D. S. Torok et al., Journal of Organic Chemistry, 1993, vol. 58, No. 25, pp. 7274-7276.
B. N. Bleckett et al., Tetrahedron, 1970, vol. 26, No. 5, pp. 1311-1313.
Y. Shigemitsu et al., Chemistry Letters, 2004, vol. 33, No. 12, pp. 1604-1605.
English language Abstract of JP 2003-277373.
Huang et al., "Selective Preparation of Oxygen-Rich [60]Fullerene Derivatives by Stepwise Addition of *tert*-Butylperoxy Radical and Further Functionalization of the Fullerene Mixed Peroxides" *J. Org. Chem*. 69:2442-2453, 2004.
Elemes et al., "Reaction of $C_{60}$ with Dimethyldioxirane—Formation of an Epoxide and a 1,3-Dioxolane Derivative" *Angew. Chem. Int. Ed. Engl*. 31(3):351-353, 1992.

*Primary Examiner*—Bernard Dentz
(74) *Attorney, Agent, or Firm*—Greenblum & Bernstein, P.L.C.

(57) ABSTRACT

Provided is a method for manufacturing fullerene 1,3-dioxolane conveniently at high yield. Fullerene 1,3-dioxolane is manufactured by reacting a fullerene oxide and a carbonyl compound in the presence of a catalyst.

14 Claims, No Drawings

METHOD FOR MANUFACTURING FULLERENE DERIVATIVES

TECHNICAL FIELD

The present invention relates to a method for manufacturing fullerene 1,3-dioxolane from fullerene oxide.

BACKGROUND TECHNIQUE

Fullerene and its derivatives have attracted attention in the fields of cluster science relating to clathrates and application to pharmaceuticals and photoelectronic devices. Of these, fullerene 1,3-dioxolane is an electron acceptor and has attracted attention as a high-functionality material.

The method of manufacturing 1,3-dioxolane by the reaction below from an epoxide and a carbonyl compound is known. The use of a Lewis acid catalyst in this reaction has been proposed.

[Chem. 1]

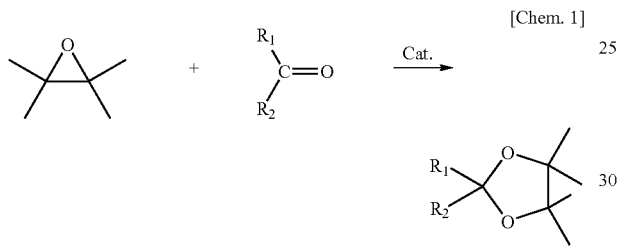

For example, the method of manufacturing 1,3-dioxolane by the following reaction employing $BF_3$ etherate as a catalyst is described in Reference 1 (B. N. Blackett, J. M. Coxon., M. P. Hartshorn, A. J. Lewis, G. R. Little and G. J. Wright, Tetrahedron, 26, 1311-1313 (1970)).

[Chem. 2]

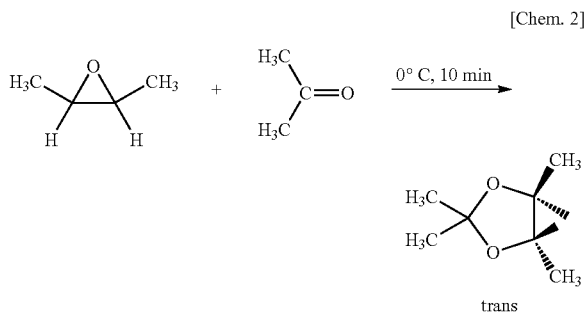

Further, the method of manufacturing 1,3-dioxolane by the following reaction using anhydrous $CuSO_4$ as a catalyst is described in Reference 2 (R. P. Hanzlik and M. Leinwetter. J. Org. Chem., 43, 438 (1978)).

[Chem. 3]

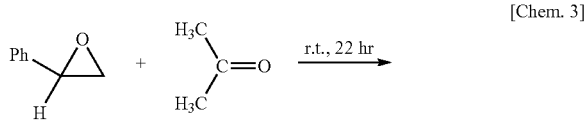

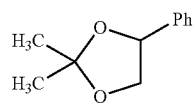

The method of manufacturing 1,3-dioxolane by the following reaction is described in Reference 3 (H. Steinbrink, Ger. Patent (DOS) 1086241, Chemische Werke Hüls AG (1959)).

[Chem. 4]

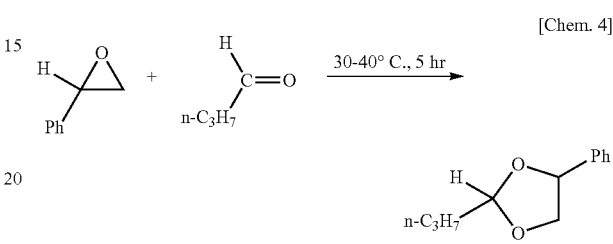

The method of manufacturing 1,3-dioxolane by the reaction is described in Reference 4 (F. Nerdel, J. Buddrus, G. Scherowsky, D. Klamann, and M. Fligge, Justus Liebig Ann. Chem. 710, 85 (1967)).

[Chem. 5]

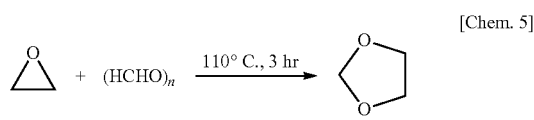

As catalysts, KSF clay is employed in Reference 3 and tetraethylammonium bromide is employed in Reference 4.

The mechanisms of the reactions described in the above-cited references are as follows. Due to the stereochemistry of products obtained by the method described in Reference 1 and based on the results of tests employing $O^{18}$ acetone, as is indicated below, it is thought that following a backside attack by the carbonyl oxygen, the CC bond is rotated, producing a second CO bond and thereby producing 1,3-dioxolane. However, in this reaction, there is a problem in that a side reaction of epoxy and aldehyde reduces the yield of 1,3-dioxolane. Further, the catalyst employed is highly hygroscopic and difficult to handle.

[Chem. 6]

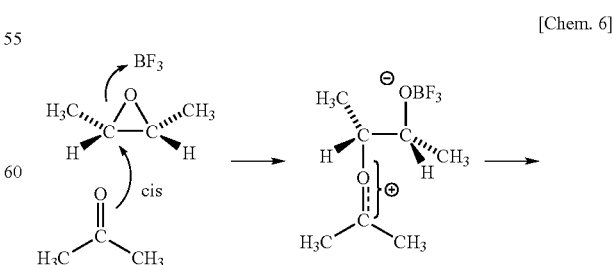

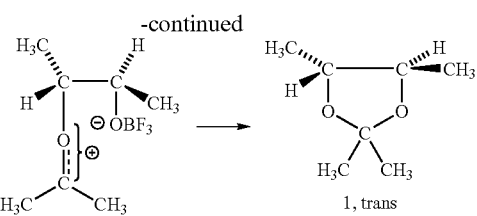

1, trans

A method for manufacturing 1,3-dioxolane by the following reaction using a pyridinium salt as a catalyst is described in Reference 5 (S-B. Lee, T. Tanaka, and T. Endo, Chem. Lett., 2019-2022 (1990)).

[Chem. 7]

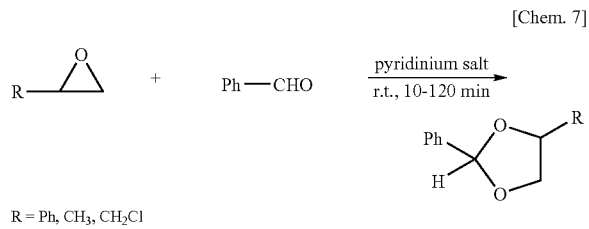

R = Ph, CH₃, CH₂Cl

The reaction mechanism of the method described in Reference 5 is presumed to be similar to that set forth above.

References 6 to 8 report methods of obtaining fullerene 1,3-dioxolane using fullerene as a starting material (Reference 6: Y. Achiba et al., Tetrahedron Lett., 34, 7629-7632 (1993); Reference 7: C. S. Foote et al., Angew. Chem. Int. Ed. 31, 351-353 (1992); Reference 8: S-H. Wu et al., J. Chem. Soc., Chem. Commun., 1995, 1071). However, in the methods described in References 6 to 8, fullerene 1,3-dioxolane is often obtained together with other fullerene derivatives. Thus, these methods do not permit the obtaining of fullerene 1,3-dioxolane with high yields. There is a further problem in that the reagents employed, such as peroxides, are difficult to handle.

DISCLOSURE OF THE INVENTION

The object of the present invention is to provide a method for manufacturing fullerene 1,3-dioxolane conveniently at high yield.

The present inventors conducted extensive research into achieving the above-stated object, resulting in the discovery that by using fullerene oxide as a starting material, it was possible to conveniently manufacture fullerene 1,3-dioxolane at high yield. The present invention was devised on this basis.
[1] A method of manufacturing fullerene 1,3-dioxolane by reacting a fullerene oxide and a carbonyl compound in the presence of a catalyst.
[2] The method of [1], wherein said catalyst is a Lewis acid catalyst.
[3] The method of [2], wherein said catalyst is an onium salt.
[4] The method of [3], wherein said onium salt is a pyridinium salt.
[5] The method of any one of [1] to [4], wherein said carbonyl compound is an aldehyde.
[6] The method of any one of [1] to [4], wherein said carbonyl compound is a ketone.

According to the present invention, fullerene 1,3-dioxolane, which is useful as a high-functionality material, can be obtained conveniently at high yield.

BEST MODE OF IMPLEMENTING THE INVENTION

The manufacturing method of the present invention is a method of production of fullerene 1,3-dioxolane by reacting a fullerene oxide and a carbonyl compound in the presence of a catalyst.

According to the manufacturing method of the present invention, fullerene 1,3-dioxolane can be obtained at high yield by convenient reaction with a carbonyl compound using a fullerene oxide as a starting material. The manufacturing method of the present invention affords the further advantage of controlling the position of the 1,3-dioxolane.

When employing fullerene as a starting material in the manner described in the techniques of above-cited References 6 to 8, it is difficult to control the position at which 1,3-dioxolane is produced. When a fullerene oxide is employed as a starting material, the 1,3-dioxolane is produced at the position of the epoxide, making it possible to control the position of the 1,3-dioxolane. Further, the present inventors have established a method of obtaining fullerene oxide in which the epoxide is present at a prescribed position (see Japanese Unexamined Patent Publication (KOKAI) No. 2003-277373). When a fullerene oxide obtained by this method is employed as a starting material, it is possible to obtain fullerene 1,3-dioxolane having 1,3-dioxolane at a prescribed position.

Further, as set forth above, in the mechanism of the reaction yielding 1,3-dioxolane from an epoxide and a carbonyl compound, it is thought that following a backside attack by the carbonyl oxygen, the CC bond is rotated, producing a second CO bond and thereby producing 1,3-dioxolane. However, with a fullerene oxide, since the fullerene is present at the position of the backside attack by the carbonyl oxygen, it is thought that the CC bond cannot be rotated by the backside attack of the carbonyl oxygen. That is, it is impossible to obtain fullerene 1,3-dioxolane from a fullerene oxide and a carbonyl compound by this reaction mechanism.

However, surprisingly, research by the present inventors revealed that it was possible to obtain fullerene 1,3-dioxolane by reacting a fullerene oxide and carbonyl compound. Further, it is possible to obtain fullerene 1,3-dioxosilane at high yield by the method of the present invention. In the method of the present invention, a reaction is conducted between a fullerene oxide and a carbonyl compound, yielding fullerene 1,3-dioxolane at high yield by a reaction mechanism thought to be different from the conventional mechanism.

The fullerene oxide employed in the present invention can be obtained by oxidizing fullerene. $C_{60}$, as well as $C_{70}$, $C_{76}$, $C_{78}$, $C_{82}$, $C_{84}$, and the like, can be employed as the starting material fullerene. The starting material fullerene can be obtained by known methods, or may be obtained in the form of a commercial product.

The fullerene can be oxidized by, for example, oxidizing fullerene $C_{60}$ with m-chloroperbenzoic acid (m-CPBA). The oxidation reaction with m-CPBA can be conducted under the following conditions, for example, Mole ratio of fullerene $C_{60}$ and m-CPBA: from 1:10 to 1:100, preferably from 1:30 to 1:60.

Reaction temperature: 80 to 120° C.

Reaction period: 1 to 60 minutes, preferably 10 to 30 minutes.

In addition to using a method employing a perbenzoic acid such as the above-described m-CPBA, the fullerene oxide can be prepared, for example, by a method employing an oxidizing agent in the form of an organic peroxide such as furan peroxide, a dioxirane compound, ozone, $P_{450}$: cytochrome oxidase, or the like.

The fullerene oxide prepared by the above method is in the form of a mixture of fullerene oxides. A fractionation process can be employed to isolate the desired fullerene oxide (monoxide, dioxide, trioxide, or the like). The fractionation process can be conducted by known methods. The fractionation process will be described below for the example of $C_{60}$ fullerene oxide.

Generally, unreacted fullerene and lower and higher epoxides are mixed with the fullerene oxide. For example, when a mixture of fullerene oxides is subjected to HPLC, various fragments are present. The mass numbers of the individual fragments can be determined by liquid chromatography—atmospheric pressure chemical ionization—mass spectrometry ((LC-APCI-MS): high performance liquid chromatography connected to an atmospheric pressure chemical ionization mass spectroscope), for example.

For example, a fraction containing only a desired epoxide (monoxide, dioxide, trioxide, or the like) can be separated from a mixture of fullerene oxides with silica gel by the above LC-APCI-MS. Specifically, the mixture of fullerene oxides is placed on a column packed with silica gel and a suitable eluant is employed to sequentially elute individual fragments, yielding a fragment containing only the desired fullerene epoxide.

The silica gel employed is not specifically limited. However, an alkane group-bonded silica gel is desirable. Examples of alkane group-bonded silica gels include C18 (octadodecyl) group-bonded silica gel and C30 group-bonded silica gel.

Further, the eluant may be suitably selected based on the silica gel employed. However, from the perspective of a hydrophobic mobile phase, a mixed solvent of toluene and acetonitrile, a mixed solvent of toluene and methanol, a mixed solvent of ortho-dichlorobenzene and methanol, or the like may be employed. Further, reference may be made to Japanese Unexamined Patent Publication (KOKAI) No. 2003-277373 for methods of isolating isomers of fullerene oxides.

In the present invention, a fullerene oxide compound obtained by oxidizing fullerene can be employed in the reaction with a carbonyl group. However, since such a mixture will sometimes contain unreacted fullerene, this unreacted fullerene is desirably removed with a column packed with silica gel as set forth above prior to use in the reaction.

In the method of the present invention, fullerene oxide obtained by the method set forth above is reacted with a carbonyl compound in the presence of a catalyst to manufacture fullerene 1,3-dioxolane.

An aldehyde or a ketone may be employed as the carbonyl compound. The structure of the carbonyl compound can be suitably set in consideration of the physical properties (solvent solubility, compatibility with resins, and the like) of the fullerene 1,3-dioxolane that is the final product. A carbonyl compound with a cyclic carbonyl group may also be employed.

Specific examples of the aldehyde that can be reacted with the fullerene oxide include: aromatic aldehydes, aliphatic aldehydes, and alicyclic aldehydes. Examples of aromatic aldehydes include: benzaldehyde, 3- and 4-alkylbenzaldehydes (the alkyl group having 1 to 20 carbon atoms and being optionally substituted), and 3- and 4-alkoxyaldehydes (the alkoxy group comprising $C_1O$ to $C_{20}O$ and being optionally substituted). Examples of aliphatic aldehydes include: formaldehyde, acetaldehyde, and $R_1$—CHO (where $R_1$ denotes an optionally substituted alkyl group having 2 to 20 carbon atoms). Examples of alicyclic aldehydes include: cyclopentanecarbaldehyde, cyclohexanecarbaldehyde, cyclobutanecarbaldehyde, and cyclooetanecarbaldehyde. Examples of heterocyclic aldehydes include: furfural, nicotinaldehyde, 2-tetrahydrofurancarbaldehyde, and 2-thiophenecarbaldehyde.

Examples of the ketone employed in the reaction with fullerene oxide include aromatic ketones, aliphatic ketones, carbocyclic ketones, and heterocyclic ketones. Examples of aromatic ketones include: acetophenone, 3- and 4-alkyl-substituted acetophenones ($R(C_6H_4)COCH_3$, where R denotes an optionally substituted alkyl group having 1 to 20 carbon atoms), 3- and 4-alkoxy-substituted acetophenones ($RO(C_6H_4)COCH_3$, where R denotes an optionally substituted alkyl group having 1 to 10 carbon atoms), propiophenone derivatives ($R(C_6H_4)COC_2H_5$, where R denotes an optionally substituted alkyl group having 1 to 20 carbon atoms or an optionally substituted alkoxy group having 1 to 10 carbon atoms), deoxybenzoins ($R_1(C_6H_4)CH_2CO(C_6H_4)R_2$, where each of $R_1$ and $R_2$ independently denotes H, an alkyl group having 1 to 20 carbon atoms, or an alkoxy group having 1 to 10 carbon atoms), $R_1(C_6H_4)COR_2$ (where $R_1$ denotes an alkyl group having 1 to 20 carbon atoms or an alkoxy group having 1 to 10 carbon atoms, and $R_2$ denotes an alkyl group having 3 to 10 carbon atoms), and benzophenone derivatives ($R_1(C_6H_4)CO(C_6H_4)R_2$ (where each of $R_1$ and $R_2$ independently denotes H, an alkyl group with 1 to 20 carbon atoms, an alkoxy group with 1 to 10 carbon atoms, or a halogen atom). Examples of aliphatic ketones include $R_1COR_2$ (where each of $R_1$ and $R_2$ independently denotes an optionally substituted alkyl group having 1 to 20 carbon atoms), such as acetone, methyl ethyl ketone, diethyl ketone, methyl propyl ketone, ethyl propyl ketone, dipropyl ketone, methyl t-butyl ketone, and ethyl t-butyl ketone. Examples of carbocyclic ketones include cyclopentanone, cyclohexanone, cycloheptanone, cyclooctanone, indene-1-one, indanone, 9-fluorenone, anthrone, and 1-oxo-1,2,3,4-tetrahydronaphthalene. Examples of heterocyclic ketones are such compounds comprising oxygen atoms, nitrogen atoms, and sulfur atoms. Heterocyclic ketones with ester structures are preferred, examples of which are gamma-butyrolactone, delta-valerolactone, and gamma-valerolactone.

The reaction can be conducted by dissolving a fullerene oxide and carbonyl compound in a solvent and stirring the mixture in the presence of a catalyst. Here, the order in which the fullerene oxide, carbonyl compound, and catalyst are added is not specifically limited. For example, the fullerene oxide may be dissolved in solvent and the carbonyl compound and catalyst subsequently added to conduct the reaction.

The catalyst employed in the reaction can be a Lewis acid catalyst. Lewis acid catalysts that are suitable for use include: onium salts, $BF_3Et_2O$, $AlCl_3$, $SnCl_4$, $ZnCl_2$, and $FeCl_3$. Examples of onium ions forming onium salts are: pyridinium, quinolinium, isoquinolinium, phosphonium, sulfonium, and iodonium. Examples of paired anions forming salts with onium ions are $SbF_6^-$, $PF_6^-$, $BF_4^-$, $AsF_6^-$, and halogen ions. Of these, pyridinium salts are desirably employed as catalysts in the present invention. These catalysts can be synthesized by known methods. They may also be obtained in the form of commercial products. These catalysts may be employed singly or in combinations of two or more. For example, the addition of a small quantity of $BF_3Et_2O$ to systems employing an onium salt as catalyst sometimes causes the reaction to progress smoothly.

The solvent employed in the reaction is desirably one that is compatible with fullerene oxide and the catalyst. Specifically, toluene, chlorobenzene, o-dichlorobenzene, benzene 1,2,4-trimethylbenzene, and anisole may be employed among others. In the present invention, selecting the solvent best suited to the carbonyl compound employed enhances the reaction yield.

The proportions in which the fullerene oxide and carbonyl compound are mixed are desirably set so that there is an excess quantity of carbonyl compound. The mixing ratio of fullerene oxide and carbonyl compound can be, for example, fullerene oxide:carbonyl compound=1:10 to 1:1,000, preferably 1:100 to 1:300. The concentration of fullerene oxide depends on the solubility of the fullerene oxide in the solvent, and can, for example, be set to $10^{-2}$ to $10^{-4}$ M, preferably on the order of $10^{-3}$. The concentration of carbonyl compound is desirably set based on the fullerene oxide concentration so that the mixing ratio of fullerene oxide and carbonyl compound falls within the above-stated range.

The quantity of catalyst employed in the reaction can be from 1 to 50 mole percent, preferably 1 to 30 mole percent, of the fullerene oxide. The reaction temperature can be, for example, 50 to 110° C., desirably 60 to 100° C., preferably 65 to 80° C. The reaction period depends on the reaction temperature. For example, the reaction time can be from 30 minutes to 10 hours, preferably from 1 to 3 hours. The reaction can be conducted in an inert gas atmosphere such as an argon, helium, or nitrogen atmosphere.

Following the above reaction, the solvent is distilled off under reduced pressure and the residue is washed with a suitable solvent and purified by silica gel column chromatography, yielding fullerene 1,3-dioxolane. When employing fullerene dioxide as starting material, fullerene 1,3-dioxolane can be obtained. However, a mixture of fullerene mono-1,3-dioxolane and fullerene bis-1,3-dioxolane is initially obtained in the reaction. The fullerene mono-1,3-dioxolane and fullerene bis-1,3-dioxolane can be isolated by column chromatography. The same holds true when fullerene trioxide is employed as starting material. The fact that the desired fullerene 1,3-dioxolane has been obtained can be verified by mass spectrometry, FT-IR, $^{13}$C-NMR, and $^1$H-NMR.

Fullerene 1,3-dioxolane is suitable as a solar cell material. In particular, it can be employed as a bulk heteroclathrate organic thin-film solar cell material. Fullerene 1,3-dioxolane that is useful as a high-functionality material such as a solar cell material can be conveniently obtained at high yield based on the present invention.

EMBODIMENTS

The present invention is described in greater detail below through embodiments.

REFERENCE EXAMPLE 1

Preparation of Pyridinium SBF$_6$ Salt (Ib)

[Chem. 8]

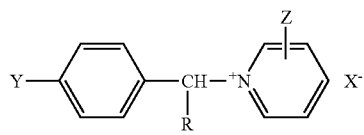

Y = OMe, R = H, Z = 4-CN, X$^-$ = SbF$_6^-$

A 4.7 g quantity of 4-methoxybenzylchloride and 3.12 g of 4-cyanopyridine were dissolved in 5 mL of acetonitrile in a 30 mL triangular Mayer flask and the solution was reacted for four days at room temperature with agitation. The acetonitrile was distilled out of the reaction solution under reduced pressure, 20 mL of diisopropyl ether was added to the residue, and the precipitate that formed was filtered out under reduced pressure, yielding 2.78 g (a yield of 36 percent) of pyridinium chloride salt. The pyridinium salt obtained was dissolved in 100 mL of water and 5.9 g of KSbF$_6$ was added. A precipitate formed immediately. The precipitate was recovered by filtration under reduced pressure, yielding 4.14 g (a yield of 84 percent, melting point 150.6-151.8° C.) of slightly yellowish pyridinium SbF$_6$ salt (Ib). The reaction scheme is given below.

[Chem. 9]

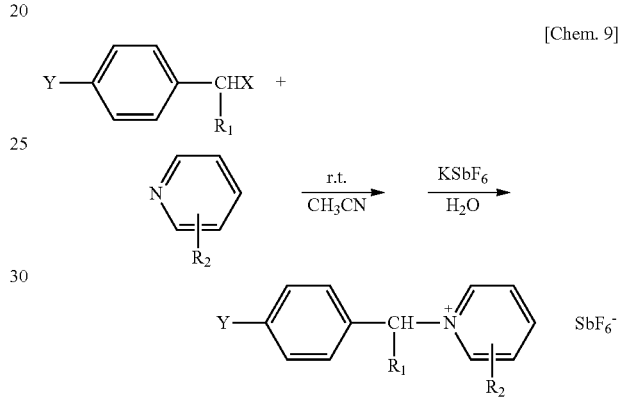

REFERENCE EXAMPLE 2

The pyridinium SbF$_6$ salts (Ia), (Ic), (Id), and (Ie) denoted below were prepared by the same method as in Reference Example 1.

[Chem. 10]

| | Y | R | Z | X$^-$ |
|---|---|---|---|---|
| Ia | OMe | H | 2-CN | SbF$_6^-$ |
| Ib | OMe | H | 4-CN | SbF$_6^-$ |
| Ic | H | CH$_3$ | 2-CN | SbF$_6^-$ |
| Id | H | H | 2-CN | SbF$_6^-$ |
| Ie | H | Ph | 4-CN | SbF$_6^-$ |

Table 1 gives the reaction conditions, yield, and physical properties of the catalyst for each reaction.

TABLE 1

Results of pyridinium salts synthesis

| Pyridinium salts | Reaction conditions | Yield (%) | Melting point (° C.), Properties |
|---|---|---|---|
| Ia | r.t., 20 days | <1 | 115.0-118.3, gray powder |
| Ib | r.t., 4 days | 30.0 | 150.6-151.8, slightly yellowish powder |
| Ic | r.t., 20 days | 15.1 | 117.8-120.3, slightly bluish powder |
| Id | r.t., 4 days | 42.3 | 150.0-155.7, colorless powder |
| Ie | r.t., 5 days | 80.3 | 156.5-159.4, colorless powder |

REFERENCE EXAMPLE 3

Preparation of Fullerene Oxides (IIa, IIb, and IIc)

Fullerene $C_{60}$ (purity of 99 percent or above, made by Frontier Carbon) was dissolved to a concentration of $1 \times 10^{-3}$ mole/L in toluene (special grade, Kanto Chemical) and 20 g/ml$^3$ of ozone/oxygen mixed gas was bubbled for 30 seconds at a rate of 1 L/minute while heating the mixture to 100° C. After cooling to room temperature while bubbling $N_2$ gas through the reaction solution, the insoluble portion was removed by filtration. Next, flash column chromatography (developing solvent:toluene/n-hexane=1:1) employing silica gel (FC40, made by Wako Pure Chemical) as packing material was employed to remove unreacted matter, yielding a mixed solution of fullerene oxides. The mixed solution of fullerene oxides was fractionated by high-performance liquid chromatography using a Docosil C22 column (made by Senshu Kagaku), and the fullerene oxides (IIa, IIb, IIc) were isolated and purified.

[Chem. 11]

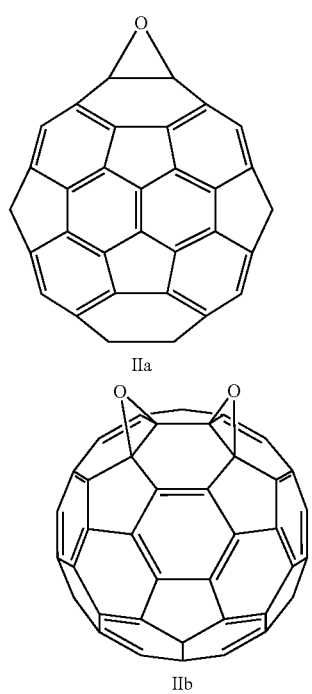

-continued

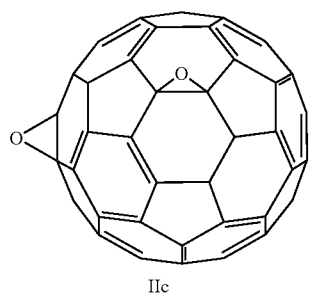

Embodiment 1

To a 10 mL eggplant-shaped flask were charged 6 mL of a toluene solution of a $2.21 \times 10^{-3}$ M concentration of fullerene monoxide IIa or fullerene dioxide IIb or IIc; 300 mg of benzaldehyde derivative $R_5(C_6H_4)CHO$; and 1.7 mg of pyridinium salt (Ia), 1.6 mg of pyridinium salt (Ic), or 1.9 mg of pyridinium salt (Ic). The flask was backfilled for 10 minutes with argon gas, after which the mixture was reacted at 75° C. The progress of the reaction was tracked by LC-MS. After elimination of the fullerene oxide had been confirmed by chromatography, the toluene was distilled out of the reaction solution under reduced pressure and the residue was washed with methanol. Subsequently, the residue was purified by silica gel chromatography, yielding fullerene 1,3-dioxolane. The chemical structure was confirmed by mass spectrometry, FT-IR, and $^{13}C$-NMR. Table 2 shows the results of the same reaction conducted in the presence of the various catalysts synthesized in Reference Example 2 and $BF_3Et_2O$ (made by Wako Pure Chemical). The structures of the 1,3-dioxolanes obtained from fullerene monoxide IIa and fullerene dioxides IIb and IIc are shown below.

[Chem. 12]

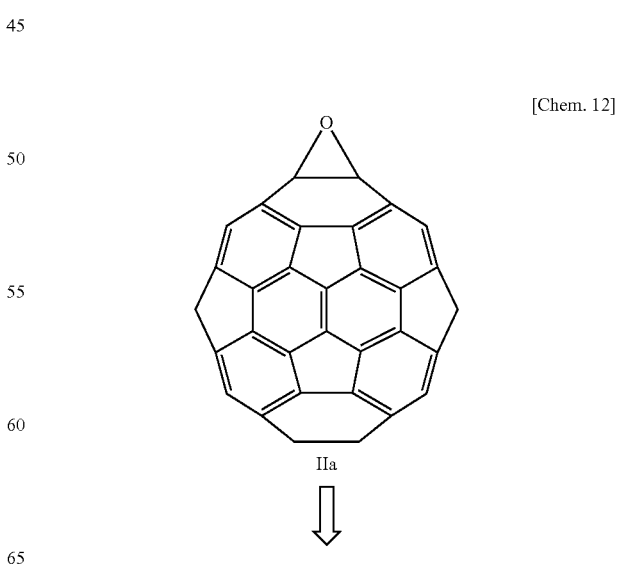

-continued

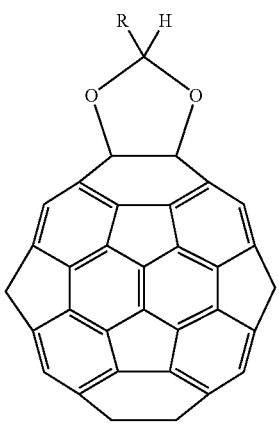

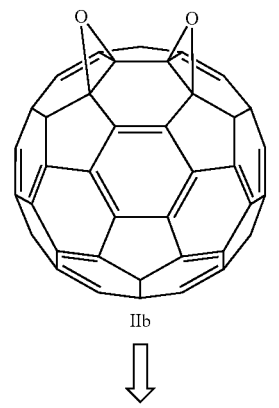

IIb

⇓

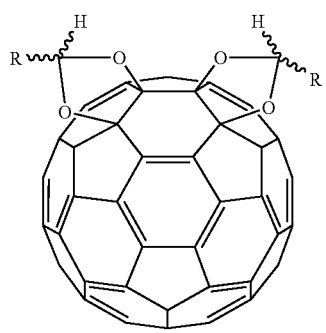

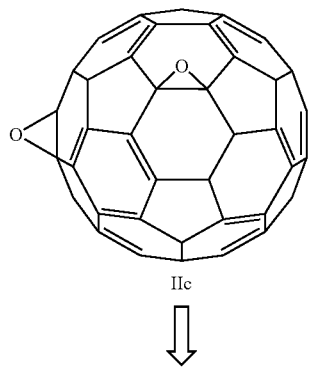

IIc

⇓

-continued

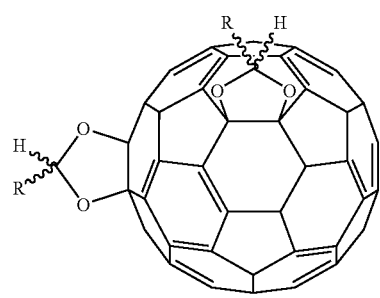

TABLE 2

Results of reactions of fullerene oxides with benzaldehyde derivatives in the presence of various catalysts

| Fullerene oxide | R$_5$ | Catalysts | Reaction time | Dioxolane Yield (%)[3] |
|---|---|---|---|---|
| IIa | n-C$_6$H$_{13}$O | Ia | 4.5 hr | 88 |
| IIb[1] | H | Ia | 3 hr | 92 |
| IIc[1] | H | Ia | 3 hr | 76 |
| IIc | C$_2$H$_5$O | Ic | 3 hr | 73 |
| IIc | n-C$_3$H$_7$O | Ic | 3 hr | 82 |
| IIc | n-C$_4$H$_9$O | Ic | 3 hr | 73 |
| IIc | n-C$_5$H$_{11}$O | Ic | 5 hr | 61 |
| IIa | n-C$_6$H$_{13}$O | Ie/BF$_3$[2] | 45 min | 79 |
| IIc | n-C$_6$H$_{13}$O | Ie/BF$_3$[2] | 30 min | 66 |
| IIa | n-C$_6$H$_{13}$O | BF$_3$[2] | 3 hr | 44 |

[1]IIb and IIc are fullerene dioxides with Cs symmetry and position isomers, each other
[2]one drop of BF$_3$Et$_2$O was added.
[3]Yield of fullerene bis 1,3-dioxolane when using fullerene monoxide IIb or IIc.

Embodiment 2

[Chem. 13]

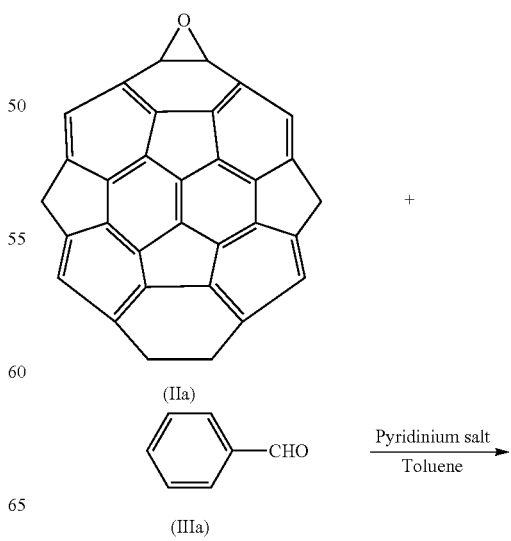

-continued

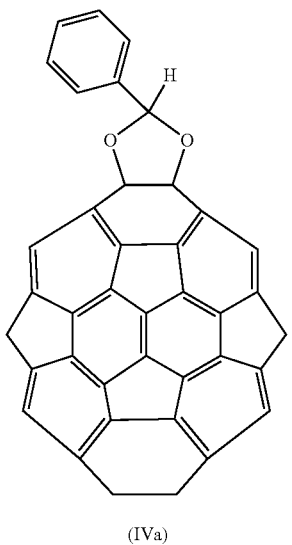

(IVa)

To a 10 mL eggplant-shaped flask were charged 6 mL of a toluene solution of a $2.21\times10^{-3}$ M concentration of fullerene monoxide (IIa), 300 mg of benzaldehyde (IIIa), and 1.7 mg of pyridinium salt (Ia). The flask was backfilled for 10 minutes with argon gas, after which the mixture was reacted at 75° C. The progress of the reaction was tracked by LC-MS. After 1 hour and 30 minutes, the elimination of (IIa) was confirmed by chromatography. The toluene was then distilled out of the reaction solution tinder reduced pressure and the residue was washed with methanol. Subsequently, the residue was purified by silica gel chromatography, yielding 10.7 mg (a yield of 91 percent) of fullerene 1,3-dioxolane (IVa). The chemical structure was confirmed by mass spectrometry, FT-IR, and $^{13}$C-NMR. Table 3 shows the results of the same reaction conducted in the presence of various catalysts.

TABLE 3

Results of synthesis of fullerene 1,3-dioxolane (IVa) in the presence of various catalysts

| | Reaction conditions | | |
|---|---|---|---|
| Catalyst/Added amount | Temperature, °C. | Time, hr | (IVa), Yield(%) |
| Ia/1.7 mg | 75 | 1.5 | 90 |
| Ib/1.7 mg | 100 | 4.0 | 70 |
| Ic/1.6 mg | 75 | 1.0 | 92 |
| Ic/1.6 mg | 60 | 4.0 | 89 |
| Id/1.6 mg | 75 | 1.0 | No reaction |
| Id[1]/1.6 mg | 75 | 0.5 | 81 |
| Ie/1.9 mg | 100 | 2.5 | 82 |
| Ic-BS[2]/1.0 mg | 100 | 1.0 | No reaction |
| Ic-BS[2,1]/1.0 mg | 75 | 0.5 | 80 |

[1] One drop of BF$_3$·etherate was added to react.
[2] Bromide of Ic

COMPARATIVE EXAMPLE

The same reaction as in Embodiment 2 was conducted for 5 hours at 75° C. in the absence of a catalyst. The reaction did not progress and the yield was 0 percent.

As will be understood from the results of Tables 2 and 3, fullerene 1,3-dioxolane can be obtained by conveniently reacting a fullerene oxide and a carbonyl compound by the method of the present invention. In particular, when a catalyst in the form of a pyridinium salt is employed, fullerene 1,3-dioxolane can be obtained at high yield. In systems in which a catalyst in the form of pyridinium salt is employed but the reaction does not proceed well, a small quantity of BF$_3$ etherate could be added to obtain fullerene 1,3-dioxolane rapidly and at high yield.

Embodiment 3

A ketone was substituted for the aldehyde derivative and the same reaction was conducted with fullerene oxide (IIa) at 75° C. to synthesize the corresponding fullerene 1,3-dioxolane. Table 4 gives the results.

TABLE 4

Synthesis of 1,3-dioxolane from ketones and fullerene oxide

| | | | Reaction | |
|---|---|---|---|---|
| Ketone | II | Catalyst | time | Dioxolane yield (%) |
| Acetophenone | IIa | Ia | 3 hr | 45 |
| Acetophenone | IIa | Ic | 30 min | 45 |
| Methyl ethyl keteone | IIa | Ic | 30 min | 44 |

As shown in Table 4, when a ketone was employed as the carbonyl compound, fullerene 1,3-dioxolane was conveniently obtained as well.

Embodiment 4

Employing the various solvents listed in Table 5, 6 mL of a solution of $2.21\times10^{-3}$ M concentration of fullerene monoxide (IIa); 300 mg of benzaldehyde, cyclohexanone, or gamma-butyrolactone; and 1 drop of BF$_3$Et$_2$O were charged to a 10 mL eggplant-shaped flask. The flask was backfilled for 10 minutes with argon gas, after which the mixture was reacted at 75° C. The progress of the reaction was tracked by the same method as in Embodiment 1. The elimination of the fullerene oxide was confirmed by chromatography, after which the reaction solution was washed 3 times with 7 percent KOH aqueous solution. The solvent was then distilled off under reduced pressure and the residue was washed with methanol. Subsequently, the residue was purified by silica gel chromatography, yielding fullerene 1,3-dioxolane. The chemical structure was confirmed by mass spectrometry, ultraviolet-visible absorbance spectrum, FT-IR, $^1$H-NMR, and $^{13}$C-NMR. The structure of the fullerene 1,3-dioxolanes obtained using cyclohexanone and gamma-butyrolactone are given below. Table 5 gives the yields of the various reactions.

[Chem. 14]

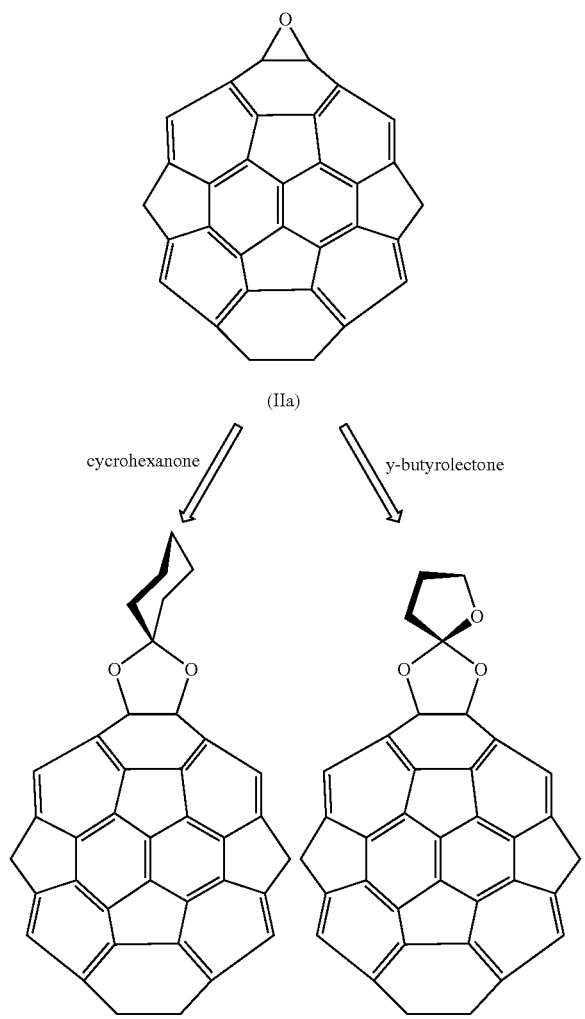

TABLE 5

Dioxolane yield obtained from fullerene oxide IIa and various carbonyl compounds in the presence of BF$_3$Et$_2$O catalyst in various reaction solvent

| Carbonyl compound | Reaction solvent | Dioxolane yield (%) |
|---|---|---|
| Benzaldehyde | Benzene | 90 |
|  | Chlorobenzene | 78 |
|  | Toluene | 45 |

TABLE 5-continued

Dioxolane yield obtained from fullerene oxide IIa and various carbonyl compounds in the presence of BF$_3$Et$_2$O catalyst in various reaction solvent

| Carbonyl compound | Reaction solvent | Dioxolane yield (%) |
|---|---|---|
|  | Anisole | 35 |
|  | 1,2,4-Trimethyl benzene | 30 |
| Cyclohexanone | Benzene | 86 |
|  | Toluene | 41 |
| Gamma-butylolactone | Benzene | 75 |

It will be understood from Table 5 that it is possible to enhance the yield by selecting the reaction solvent based on the carbonyl compound employed.

INDUSTRIAL APPLICABILITY

The fullerene 1,3-dioxolane obtained by the method of the present invention is suitable for use as a high-functionality material such as a solar cell material.

The invention claimed is:

1. A method of manufacturing fullerene 1,3-dioxolane by reacting a fullerene oxide and a carbonyl compound in the presence of a catalyst.

2. The method of claim 1, wherein said catalyst is a Lewis acid catalyst.

3. The method of claim 2, wherein said catalyst is an onium salt.

4. The method of claim 3, wherein said onium salt is a pyridinium salt.

5. The method of claim 1, wherein said carbonyl compound is an aldehyde.

6. The method of claim 1, wherein said carbonyl compound is a ketone.

7. The method of claim 2, wherein said carbonyl compound is an aldehyde.

8. The method of claim 3, wherein said carbonyl compound is an aldehyde.

9. The method of claim 4, wherein said carbonyl compound is an aldehyde.

10. The method of claim 2, wherein said carbonyl compound is a ketone.

11. The method of claim 3, wherein said carbonyl compound is a ketone.

12. The method of claim 4, wherein said carbonyl compound is a ketone.

13. The method of claim 1, wherein said carbonyl compound is a lactone.

14. The method of claim 1, wherein said fullerene 1,3-dioxolane is produced at a yield of 70-90%.

* * * * *

UNITED STATES PATENT AND TRADEMARK OFFICE
CERTIFICATE OF CORRECTION

PATENT NO. : 7,671,219 B2
APPLICATION NO. : 11/569571
DATED : March 2, 2010
INVENTOR(S) : Y. Shigemitsu et al.

It is certified that error appears in the above-identified patent and that said Letters Patent is hereby corrected as shown below:

Title Page, Item (73) at column 1, line 7 (Assignee) on the face of the printed patent, delete "Institute of Medicinal Molecular Design, Inc., Tokyo (JP)" should be --RIKEN, Saitama (JP)--.

Signed and Sealed this

Thirteenth Day of July, 2010

David J. Kappos
*Director of the United States Patent and Trademark Office*